(12) United States Patent
Miller et al.

(10) Patent No.: US 9,445,058 B2
(45) Date of Patent: Sep. 13, 2016

(54) METHOD FOR VIDEO PROCESSING USING A BUFFER

(71) Applicant: INTUITIVE SURGICAL OPERATIONS, INC., Sunnyvale, CA (US)

(72) Inventors: Brian Edward Miller, Los Gatos, CA (US); Charles Vigue, Subic (PH)

(73) Assignee: Intuitive Surgical Operations, Inc, Sunnyvale, CA (US)

( * ) Notice: Subject to any disclaimer, the term of this patent is extended or adjusted under 35 U.S.C. 154(b) by 471 days.

(21) Appl. No.: 13/891,838

(22) Filed: May 10, 2013

(65) Prior Publication Data

US 2013/0300846 A1 Nov. 14, 2013

Related U.S. Application Data

(60) Provisional application No. 61/646,597, filed on May 14, 2012.

(51) Int. Cl.
| | | |
|---|---|---|
| G06F 3/00 | (2006.01) |
| H04N 7/18 | (2006.01) |
| H04N 7/01 | (2006.01) |
| A61B 1/00 | (2006.01) |

(52) U.S. Cl.
CPC ........... *H04N 7/183* (2013.01); *A61B 1/00009* (2013.01); *H04N 7/01* (2013.01); *H04N 7/0127* (2013.01)

(58) Field of Classification Search
CPC ...... H04N 7/183; H04N 7/01; H04N 7/0127; A61B 1/00009
See application file for complete search history.

(56) References Cited

U.S. PATENT DOCUMENTS

| | | | | |
|---|---|---|---|---|
| 5,754,241 | A  * | 5/1998 | Okada et al. ............ | 375/240.05 |
| 5,982,431 | A  * | 11/1999 | Chung ..................... | 375/240.01 |
| 8,797,457 | B2 * | 8/2014 | Stevens ..................... | G09G 5/39 |
| | | | | 345/3.2 |
| 2006/0104345 | A1* | 5/2006 | Millar et al. ............. | 375/240.01 |
| 2006/0268912 | A1* | 11/2006 | Read .............................. | 370/412 |
| 2009/0270678 | A1* | 10/2009 | Scott et al. ................... | 600/109 |
| 2009/0313676 | A1* | 12/2009 | Takeshima et al. .......... | 725/119 |
| 2010/0178026 | A1* | 7/2010 | Ogasawara ..................... | 386/66 |
| 2012/0092443 | A1* | 4/2012 | Mauchly ................... | 348/14.12 |
| 2012/0257071 | A1* | 10/2012 | Prentice ..................... | 348/220.1 |

FOREIGN PATENT DOCUMENTS

CN          101911685 B  *  6/2012  ............... H04N 5/00

OTHER PUBLICATIONS

Series H: Audiovisual and Multimedia Systems, Infrastructure of Audiovisual Services—Coding of Moving Video, Advanced Video Coding for Generic Audiovisual Services, Recommendation ITU-T H.264, Jun. 2011.

* cited by examiner

*Primary Examiner* — Henry Tsai
*Assistant Examiner* — Jing-Yih Shyu

(57) ABSTRACT

A method for processing video can include storing input video frame data at a video data buffer and outputting the stored video frame data from the video data buffer at an output video frame rate based on at least an amount of video frame data stored at the video data buffer.

18 Claims, 11 Drawing Sheets

US 9,445,058 B2

METHOD FOR VIDEO PROCESSING USING A BUFFER

This application claims the benefit of U.S. Provisional Application No. 61/646,597, filed May 14, 2012, which is incorporated by reference herein in its entirety.

TECHNICAL FIELD

The present disclosure is generally directed to processing video data. More particularly, aspects of the present disclosure relate to methods and systems of processing video data captured at a surgical site for use in remotely-controlled surgical systems.

INTRODUCTION

Minimally invasive surgical techniques generally attempt to perform surgical procedures while minimizing damage to healthy tissue. Remotely-controlled surgical instruments can be used to perform various minimally invasive surgical procedures. In robotic surgical systems, a surgeon manipulates various input devices at a surgeon console (sometimes referred to herein as master inputs) to control one or more corresponding remotely-controlled surgical instruments at a remote surgical site. The remote surgical site can be observed via a video display (e.g., monitor), that displays changes captured at the site by an endoscopic camera, also mounted at the patient side cart and manipulatable by input at the surgeon side console. The input at the surgeon console is communicated to a patient side cart that interfaces with the remotely-controlled surgical instruments, where a corresponding teleoperated/telerobotic manipulation of the surgical instrument occurs to perform a surgical and/or other procedure on the patient at the remote surgical site.

Minimally invasive, remotely-controlled surgical instruments may be used in a variety of operations and may have various configurations. Many such instruments include, but are not limited to, a surgical end effector mounted at a distal end of a long shaft that is configured to be inserted (e.g., laporoscopically or thoracoscopically) through an opening (e.g., body wall incision, natural orifice, etc.) to reach a remote surgical site within a patient. In some instruments, an articulating wrist mechanism is mounted to the distal end of the instrument's shaft to support the end effector and alter an orientation (e.g., pitch and/or yaw) of the end effector with reference to the shaft's longitudinal axis.

Telerobotically controlled end effectors may be configured to perform various functions, including any of a variety of surgical procedures that are conventionally performed in either open or manual minimally invasive surgical procedures. Examples include, but are not limited to, sealing, cutting, cauterizing, ablating, suturing, stapling, etc. To control motion of an end effector, servo-actuators (e.g., servo motors) can be used to transmit force or torque to various components of a patient side manipulator down the instrument shaft and to the end effector.

When performing a surgical procedure at a remote site, for example either via a telerobotically controlled surgical system or other remotely-controllable instrument (e.g., conventional manual laporoscopy or endoscopy procedures), it may be desirable for video images captured at the remote surgical site to arrive at the display with relative regularity and with minimal or no latency between capturing and displaying. It also may be desirable, however, to provide relatively high-quality images at the video display. In this way, a video processing and display system at the surgeon side console may display uninterrupted real-time video of the remote surgical site, and thus provide a surgeon with a clear and accurate image of the remote surgical site. However, if images captured at the remote surgical site do not arrive at the surgeon console with regularity because, for example, video data including the images experiences a network-based delay, the video processing and display system might not display uninterrupted real-time video of the remote surgical site.

Maintaining a predetermined latency between the recording of an image at the remote surgical site and the video processing and display system at the surgeon console may reduce or eliminate video display interruptions if the predetermined latency exceeds most or all data delays (e.g., network-based delays). However, in circumstances where low or no latency is desired (e.g., remotely-controlled surgical systems), a predetermined latency necessary to reduce or eliminate interruptions may exceed a latency considered desirable for such circumstances.

There exists a need, therefore, to provide a remotely/telerobotically controlled surgical system that can display substantially uninterrupted video images of a remote surgical site with low latency at a surgeon console display. In other words, there exists a need to provide a video processing system and method that provides low latency (useful for applications in which substantially real-time display is desired) as well as providing high fidelity with the images captured at the site.

SUMMARY

The present disclosure solves one or more of the above-mentioned problems and/or demonstrates one or more of the above-mentioned desirable features. Other features and/or advantages may become apparent from the description that follows.

In accordance with at least one exemplary embodiment, the present disclosure contemplates a method for processing video that includes storing input video frame data at a video data buffer and outputting the stored video frame data from the video data buffer at an output video frame rate based on at least an amount of video frame data stored at the video data buffer.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as disclosed or claimed. The claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

DETAILED DESCRIPTION

Figure 1:
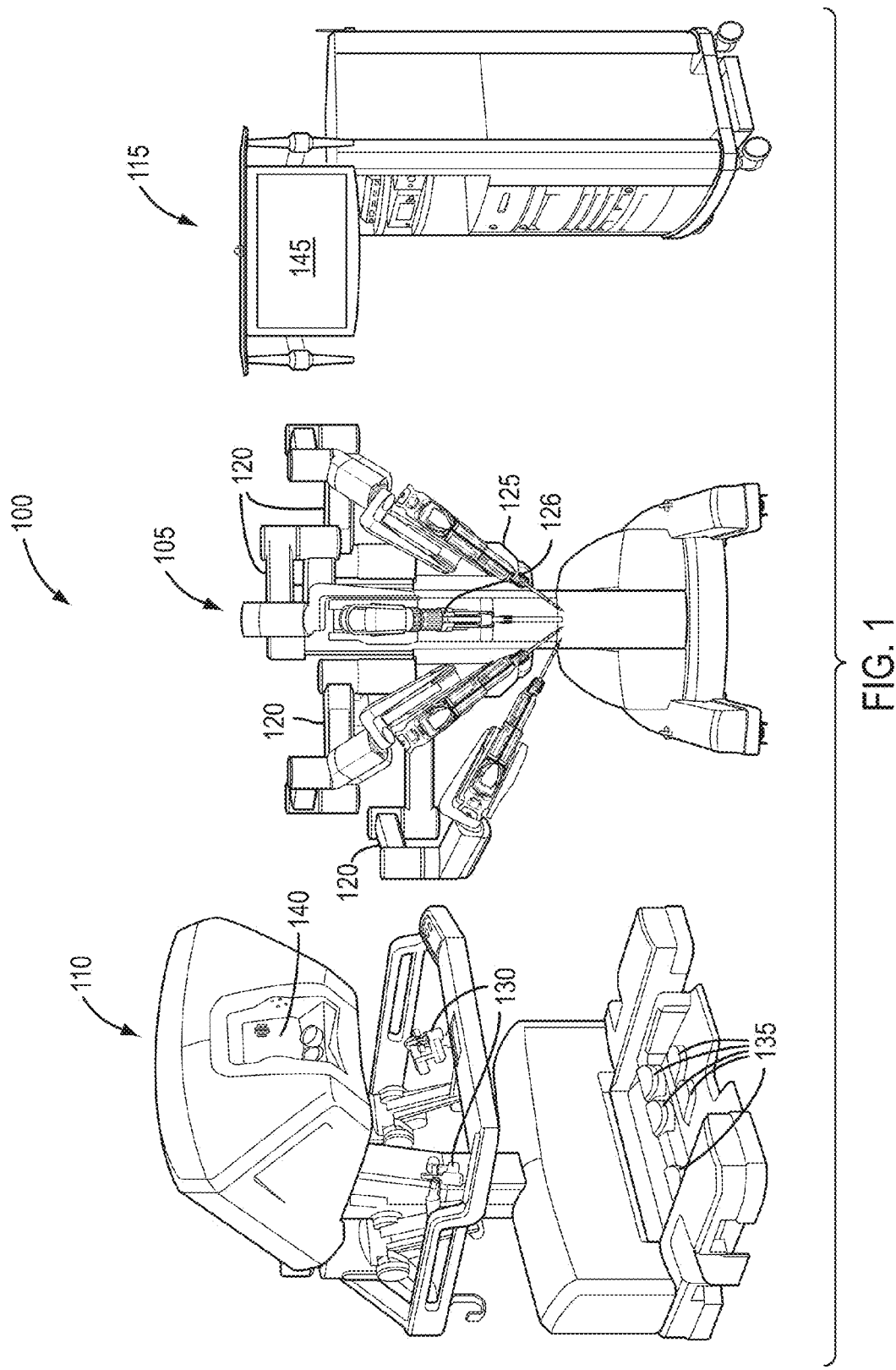
FIG. 1 is a diagrammatic view of an exemplary embodiment of a minimally invasive robotic surgical system.

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates a method and system of processing real-time video data for video applications, and in particular, real-time video data for use in remotely-controlled surgical systems. Various exemplary embodiments, therefore, are directed to a method and system for providing high fidelity (e.g., high fidelity with captured images) and relatively low latency video reproduction at a display of video images captured at a remote surgical site by, for example, an endoscopic camera.

Although the exemplary embodiments and description below focus mainly on reproduction of real-time video data for performing remotely-controlled surgical applications, the principles of the exemplary embodiments could be applied in other video processing applications, such as, video reproduction of any video data intended to be displayed in real-time, as well as non-real-time video data streamed from a remote storage location.

In accordance with at least one exemplary embodiment, the present disclosure contemplates a video processing system that includes a video data buffer, first video data stored in the video data buffer, and second video data output from the video data buffer at an output rate that varies based on an amount of the first video data stored in the video data buffer.

In accordance with at least another exemplary embodiment, the present disclosure contemplates a video processing system that includes a video data buffer, a video frame display interface logically coupled to the video data buffer to receive stored video frame data from the video data buffer, and a processor logically coupled to the vide data buffer and the video frame data display interface. The processor can be configured to receive information about the amount of video frame data stored in the video data buffer, calculate an output video frame rate to output the stored video frame data from the video data buffer, and output the stored video frame data to the video frame display interface at the output video frame rate.

A method for processing video in accordance with various exemplary embodiments can include, among other things, outputting stored video frame data from the video data buffer at an output video frame rate that is based at least in part on an amount of video frame data stored at the video data buffer.

With reference to FIG. 1, a diagrammatic view of an exemplary embodiment of a minimally invasive robotic surgical system 100 is depicted. Surgical system 100 includes a patient side cart 105, a surgeon console 110, and an electronics/control console 115. It is noted that the system components in FIG. 1 are not shown in any particular positioning and can be arranged as desired, with patient side cart 105 being disposed relative to the patient so as to affect surgery on the patient. A non-limiting, exemplary embodiment of a robotic surgical system such as system 100 is a da Vinci® Si (model no. IS3000) commercialized by Intuitive Surgical, Inc. of Sunnyvale, Calif.

Robotic surgical system 100 is used to perform minimally invasive robotic surgery by interfacing with and controlling a variety of surgical instruments. The patient side cart 105 includes various arms 120 for holding, positioning, and manipulating the various surgical instruments and/or associated tools. As shown in FIG. 1, an arm 120 of patient side cart 105 is configured to interface with and control a remotely-controlled surgical instrument 125, which may include, for example, an end effector (not shown) and/or an endoscope (not shown).

Surgeon console 110 receives inputs from a surgeon by various input devices, including but not limited to, for example, master grip input mechanisms 130 and foot pedals 135. Through the input devices, the surgeon console 110 serves as a master controller by which the instruments mounted at the patient side cart 105 act as a slave to implement any desired motions of the surgical instrument(s), and accordingly perform a desired surgical procedure. However, surgical system 100 is not limited to receiving inputs at the surgeon console 110, and inputs may be received at any device which can be configured to realize a manipulation of the surgical instrument(s) at the patient side cart 105. For example, a surgical instrument at the patient side cart 105 may be manipulated at the patient side cart 105, through the surgeon console 110 in combination with other surgical instrument support device, or entirely through another surgical support device, as a result of inputs received from the user, e.g., the surgeon.

Surgeon console 110 may further include an electronic data processing system, including a processor, which may be configured to receive and process inputs from the surgeon console 110, or from any other surgical instrument support device, and control the manipulation of one or more surgical instruments at the patient side cart 105 based on such inputs. However, elements of such electronic data processing system may be provided elsewhere within surgical system 100.

Electronics/control console 115, receives and transmits various control signals to and from the patient side cart 105 and the surgeon console 110, and can transmit light and process images (e.g., from an endoscopic camera at the patient side cart 105) for display, such as, e.g., display 140 at the surgeon console 110 and/or on a display 145 associated with the electronics/control console 115. Those having ordinary skill in the art are generally familiar with such electronics/control consoles of remotely-controlled surgical systems.

In various exemplary embodiments, patient side cart 105 is positioned proximate to a patient, and one or more surgical instruments 125 remotely controlled from, for example, surgeon console 110, receives inputs from the surgeon console 110 via various master input devices, such as, for example, hand-held grip input levers (not shown) of a master grip input mechanism 130, foot pedals 135, and camera control mechanism (not shown). In an exemplary embodiment, foot pedals 135 may be used to send signals to perform a sealing and/or cutting operation of a remotely-controlled surgical instrument and the hand-held grip input levers of master grip input mechanism 130 may be used to send signals to control movement of the of a remotely-controlled surgical instrument (e.g., pitch/yaw movement). A camera control mechanism may be used to send signals to an endoscopic camera manipulator ("ECM") embedded at one of arms 120, and to a endoscopic camera 126, to control various aspects related to capturing and processing video of a surgical site, such as the position/orientation of the camera with respect to the surgical site, zoom of the camera lens, focus of the camera lens, etc. Those having ordinary skill in the art are generally familiar with the use of such teleoperated robotic surgical systems to provide input from a surgeon at a surgeon console to ultimately effect operation of a surgical instrument interfacing with a patient side cart.

Figure 2:
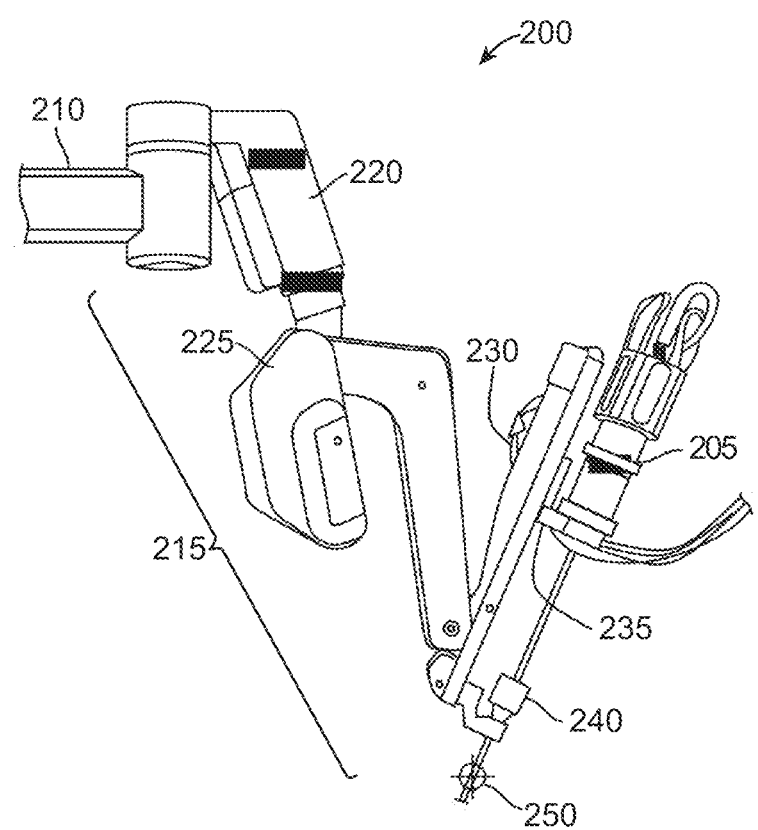
FIG. 2 is a perspective view of a portion of a camera arm of a minimally invasive robotic surgical system in accordance with at least one exemplary embodiment of the present disclosure.

FIG. 2 illustrates a side elevation view of a portion of a camera arm 200 with an illustrative endoscopic camera 205 mounted therein according to an exemplary embodiment of the present disclosure. In the exemplary embodiment, camera arm 200 includes a set-up portion 210 and a manipulator portion (ECM) 215. ECM 215 includes a yaw motion actuator 220, a pitch motion actuator 225, and an input/output motion actuator 230. Endoscopic camera 205 is mounted on carriage assembly 235 and its distal end is received through a mount 240. ECM 215 moves endoscopic camera 205 around and through a remote center of motion 250. A camera arm according to an exemplary embodiment may include more or less elements than those illustrated in FIG. 2. For example, a camera arm according to the present disclosure may include more, less, or none of the motion actuators set forth in FIG. 2 without departing from the scope of the present disclosure. Furthermore, the present disclosure is not limited to remote-controlled surgical systems, and thus, a camera according to the present disclosure may not be attached to a camera arm as that shown in FIG. 2.

In operation of a robotic surgical system as the one described with reference to FIGS. 1 and 2, a surgical procedure may include making one or more incisions in a patient's body. Such incisions are sometimes referred to as "ports", a term which may also mean a piece of equipment that is used within such an incision. In some surgical procedures, several instrument and/or camera ports may be used to provide access to and imaging of a surgical site.

Figure 3:
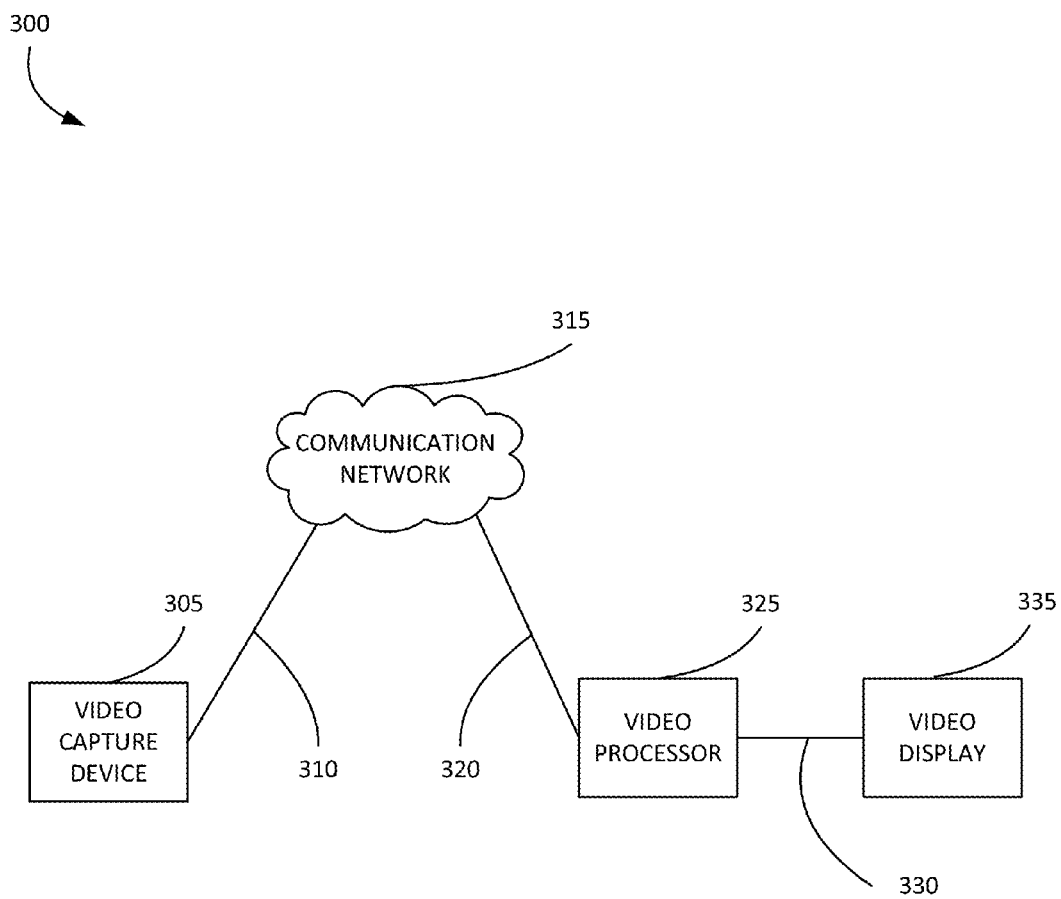
FIG. 3 is a functional block diagram of a video processing system in accordance with at least one exemplary embodiment of the present disclosure.

With reference now to FIG. 3, a functional block diagram 300 of an exemplary embodiment of a video processing system in accordance with the present disclosure is depicted. Block 305 represents a video capture device 305 according to the present disclosure. In addition to capturing images, video capture device 305 may include encoding functionality for encoding the captured images in one or more encoding formats, such as, for example, the H.264 video coding format (International Telecommunication Union (ITU) Telecommunication Standardization Section (ITU-T) Recommendation/Standard H.264 (also known as International Organization for Standardization/International Electrotechnical Commission (ISO/IEC), Moving Picture Expert Group version 4 (MPEG-4) Advanced Video Coding (AVC) standard (or ISO/IEC MPEG-4 AVC standard))).

Video capture device 305 is logically coupled to communication network 315 through communication link 310, and communication network 315 is logically coupled to video processor 325 through communication link 320. Thus, data communication between video capture device 305 and video processor 325, such as, for example, encoded images, may be realized through at least communication links 310 and 320 and communication network 315.

Video processor 325 is logically coupled to video display 335 through communication link 330. Video display 335 may be realized, for example, by a display device such as display 140 at the surgeon console 110 of FIG. 1 and/or a display 145 associated with the electronics/control console 115 of FIG. 1. Upon receipt of encoded images from video capture device 305, video processor 325 decodes the encoded images for presentation on video display 335, and provides the images to video display 335 through communication link 330.

In various exemplary embodiments, communication links 310, 320, and 330 may include a wired link, a wireless link, or a combination thereof. A wired link may comprise metal, glass, air, space, or some other material as the transport media, and communication therein may be realized through a communication protocol such as, for example, Internet Protocol (IP), Ethernet, or some other communication format with which those having ordinary skill in the art are familiar, or combinations thereof. Communication network 315 may include a router, a computer system, or any other element capable of logically interconnecting multiple devices, and may be embodied as a local area network (LAN), an intranet, a wide area network (WAN), a carrier network, the internet, or some other type of communications network, or combinations thereof. Thus, video processor 325 may be located proximate, within a few feet, or within miles of video capture device 305, without departing from the teachings disclosed herein.

Video capture device 305 includes circuitry and other components for capturing images and transmitting data corresponding to such images to video processor 325 through communication network 315. For example, but not as limitation, video capture device 305 may include an endoscopic camera, such as endoscopic camera 205 of FIG. 2. Other examples of a video capture device 305 can include, but are not limited to, an external room camera for capturing images outside the patient, and various devices used for medical imaging, such as, ultrasound imaging, magnetic resonance imaging (MRI), and computed tomography (CT) imaging capture devices.

Video processor 325 includes circuitry for processing video data received from video capture device 305 through communication network 315 and for providing processed video data to a display device such as video display 335, as will be explained in further detail below.

In the exemplary embodiment of FIG. 3, image data captured at video capture device 305 may be transmitted to video processor 325 and displayed approximately as the data is captured (e.g., in "real-time") on video display 335 through communication network 315. In such a case, it is desirable to minimize the effects of communication delays caused by, for example, congestion at the communication network 315, while maintaining relatively low latency between the capturing of an image frame at video capture device 305 and the display of the video frame on video display 335. It also is desirable to provide high fidelity images to those that are captured that appear at the display in a relatively smooth, continuous manner with minimal jitter or other appearance of noise.

According to various exemplary embodiment of the present disclosure, image data from video capture device 305 is stored at a video data buffer (not shown) accessible to video processor 325, and stored data is provided from the video data buffer to video display 335 at an output video frame rate based on at least an amount of video frame data stored at the video data buffer.

Figure 4:
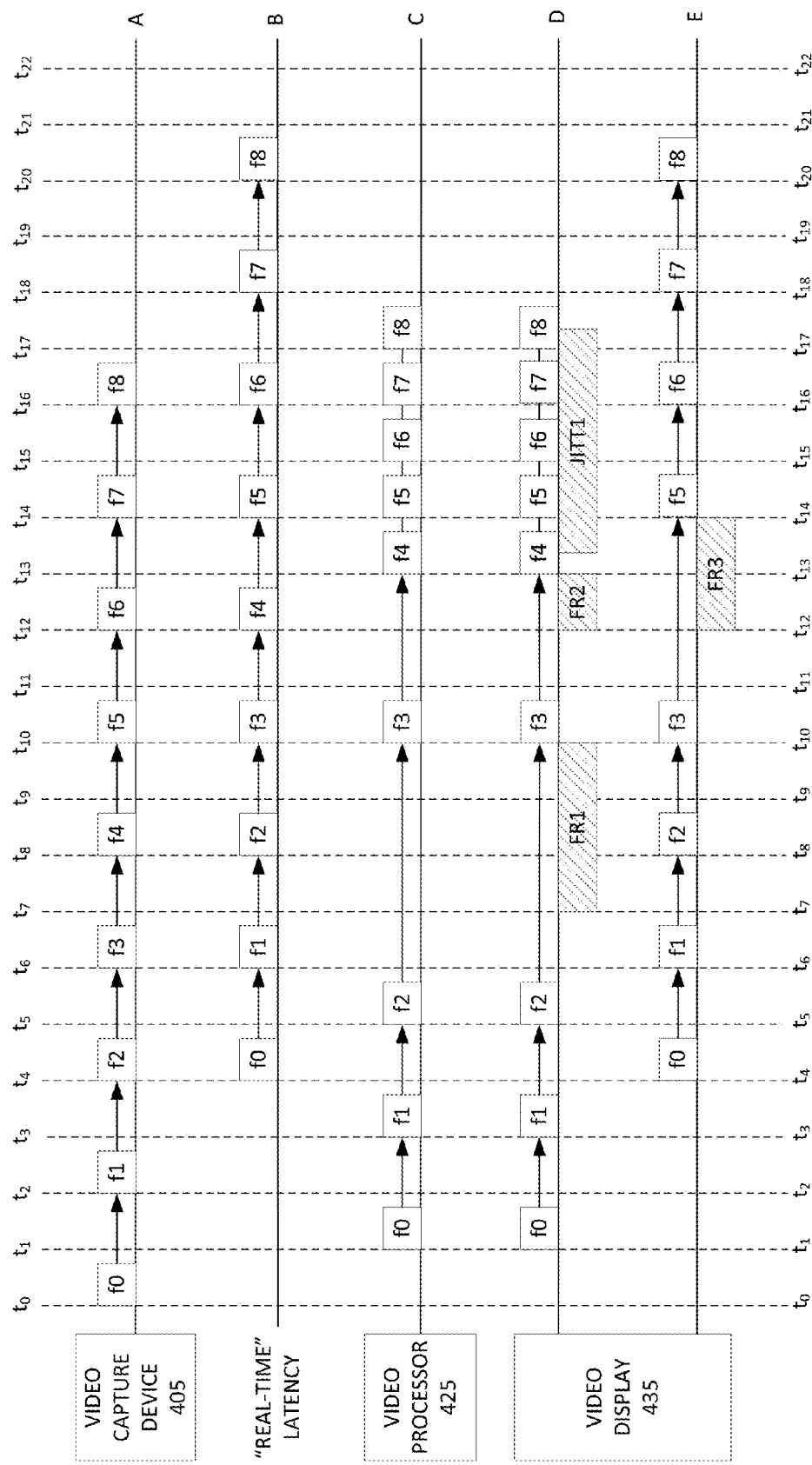
FIG. 4 is a timing diagram for schematically illustrating concepts related to the present disclosure.

To illustrate various concepts related to the present disclosure, FIG. 4 is a schematic timing diagram for depicting the timing of capturing and displaying image data. Specifically, FIG. 4 illustrates the transmission of image frames (f0-f8) for a conventional video processor 425 so as to demonstrate certain drawbacks of conventional video processors. Units $t_{0-22}$ represent units of time. The image frames may be generated by an image capture system such as, for example, video capture device 405, at a remote surgical site via a remotely-controlled surgical system camera (e.g., endoscopic camera), and transmitted at a predetermined rate from the video capture device 405 (see FIG. 4, Abscissa A; a frame is transmitted every 2 time units ($t_n$, $t_{n+2}$, $t_{n+4}$, ... )).

In certain applications, such as remotely-controlled surgery, it is desirable that video images captured at a remote site are received at a remote controlling site within a relatively short latency period from the time it was captured so as to provide "real-time" display as the images are captured. Abscissa B illustrates an exemplary real-time arrival of image frames f0-f8 from video capture device 405 to an exemplary video processor/display device (for purposes of the present discussion, a period of four time units (t) is considered a short/real-time latency period). In various embodiments, a latency that is associated with real-time display of captured images can range from about zero to about 1.5 seconds. However, those having ordinary skill in the art would understand that the desired latency acceptable to achieve a real-time display may depend on the desired application, network conditions, etc.

In operation, if transmission of image frames from video capture device 405 to video processor 425 is delayed for any reason (for example, due to congestion in a communication network along a path between video capture device 405 and video processor 425), video processor 425 may not receive each image frame in time to provide them to a video display (video display 435 in FIG. 4), for display in real-time (i.e., within a relatively small latency). This may decrease image quality by creating, for example, image freeze and/or image jitter. Image freeze relates to the display of an image frame on a display device for a noticeably long period of time, causing the video display to seem as if it has paused. Image jitter relates to the display of image frames on a display device at rates which notably deviate from the rate at which the image frames were captured. For purposes of the present discussion, image jitter refers to the result of displaying image frames at a rate noticeably faster from the rate at which the image frames were captured.

Abscissa C illustrates an exemplary timing at which image frames f0-f8 may arrive at video processor 425 from video capture device 405. In Abscissa C image frames are shown to experience various latencies. For example, video frames f1 and f2 arrive at video processor 425 with a latency of two time units, which is the set desired latency, whereas video frames f3 and f4 arrive at video processor 425 with a latency of four and five time units, respectively. For simplicity, frames are being shown as arriving at the beginning of a time unit. However, a person having ordinary skill in the art would understand that arrival of frames may occur at any time during a time period.

Abscissas D and E illustrate certain drawbacks associated with video processor 425 when receiving image frames f0-f8 as illustrated in Abscissa C. With reference to Abscissa D, it illustrates the display of image frames f0-f8 if video processor 425 is configured to provide received image frames to video display 435 as they become available. For simplicity, image frames f0-f8 are shown as if provided to, and displayed on, display device 435 immediately after being received, but a person having ordinary skill in the art would understand that some processing and transfer delay may occur between an image being received by video processor 425 and displayed on video display 435.

Abscissa D illustrates that under the provide-as-available configuration, the video displayed at video display 435 may experience image freeze and/or image jitter. In particular, image freeze may occur when video processor 425 does not receive a next image frame in time to maintain a smooth real-time video display. In such a case, a conventional video processor, such as video processor 425, may control video display 435 to maintain a current image frame displayed until the next image frame is available for display. Thus, the video displayed at video display 435 would appear to "freeze" while video processor 425 waits for the next image frame, which may be particularly undesirable in real-time applications such as, for example, remotely-controlled surgery. Abscissa D illustrates image freeze periods "FR1" of a length of three time units between time units $t_7$ and $t_{10}$, and "FR2" of a length of one time unit at time unit $t_{12}$. Note that, with respect to FR1, image frame f3 would ideally be displayed at time unit $t_7$ (2 time units after the display of f2). However, since image frame f3 does not arrive at video processor 425 until time period $t_{10}$, image frame f2 remains displayed until time period $t_{10}$ (3 time units longer than desired). Accordingly, video displayed to the user would freeze while displaying image frame f2.

Still with reference to Abscissa D, image jitter may occur when image frames arrive at video processor 425 in bursts, resulting in the display of several frames at a noticeably fast rate. Under the provide-as-available configuration illustrated in Abscissa D, image frames arriving as "bursts" are provided to video display 435 and shown to the user at an image frame rate which may be significantly and noticeably faster than the image frame rate at which the images were recorded, which may be particularly undesirable in real-time applications such as, for example, remotely-controlled surgery. Abscissa D illustrates image jitter period "JITT1" between time units $t_{14}$ and $t_{17}$. In particular, during image jitter period JITT1, image frames f4-f8 are provided to video display 435 at a rate of one image frame per time unit, which is twice the rate at which the image frames were captured.

As illustrated in Abscissa D, under the provide-as-available configuration, receiving image frames at video processor 425 as illustrated in Abscissa C would cause both image freeze (FR1 and FR2) and image jitter (JITT1). Although in this configuration all received image frames may be displayed, the illustrated image freezes and/or image jitter may affect the quality of the real-time video, which may be particularly undesirable in applications where both image quality and display in real-time (low latency) are desirable such as, for example, remotely-controlled surgery.

Abscissa E illustrates the display of image frames f0-f8 if video processor 425 is configured to provide video display 435 only with those image frames which arrive within their scheduled real-time latency period. For illustration purposes, it will be assumed that their scheduled real-time latency period corresponds to the timing illustrated in Abscissa B. Image frames which do not arrive within the scheduled latency period are discarded (i.e., not provided to video display 435). Again, for simplicity, image frames are shown as if displayed on video display 435 immediately after being received, but a person having ordinary skill in the art would understand that some processing and transfer delay may occur between an image being received by video processor 425 and displayed on video display 435.

Under the processing of image frames illustrated in Abscissa E, the video displayed at video display 435 may experience image freeze, particularly when images arrive to video processor 425 delayed. For example, as illustrated in Abscissa E, video processor 425 may provide image frames f0 to f3 to video display 435 at their scheduled time for display when the image frames arrive at video processor 425 before they are scheduled to be displayed as set forth in Abscissa B. However, video processor 425 does not provide image frame f4 to video display 435 because this image frame did not arrive at video processor 425 within its scheduled time, that is, it arrived at video processor 425 after it was scheduled to be displayed as set forth in Abscissa B. As illustrated in Abscissa E, the dropping of image frame f4 causes image freeze period FR3, which extends from time period $t_{12}$ to time period $t_{14}$, at which time image frame f5 arrives at video processor 425 in time to be displayed at its scheduled time (i.e., time period $t_{14}$).

Accordingly, video displayed to the user would appear to have paused while displaying image frame f3 for four time units, instead of the intended two time units. Moreover, the discarding of image frame f4 also may affect video quality, as there might not be a smooth visual transition between image frame f3 and image frame f5. This also results in a lower fidelity of the displayed images with the captured images.

Various exemplary embodiments in accordance with the present disclosure attempt to address the issues illustrated in both Abscissas D and E which are undesirable in real-time applications, and particularly, in remotely-controlled surgical systems.

Figure 5:
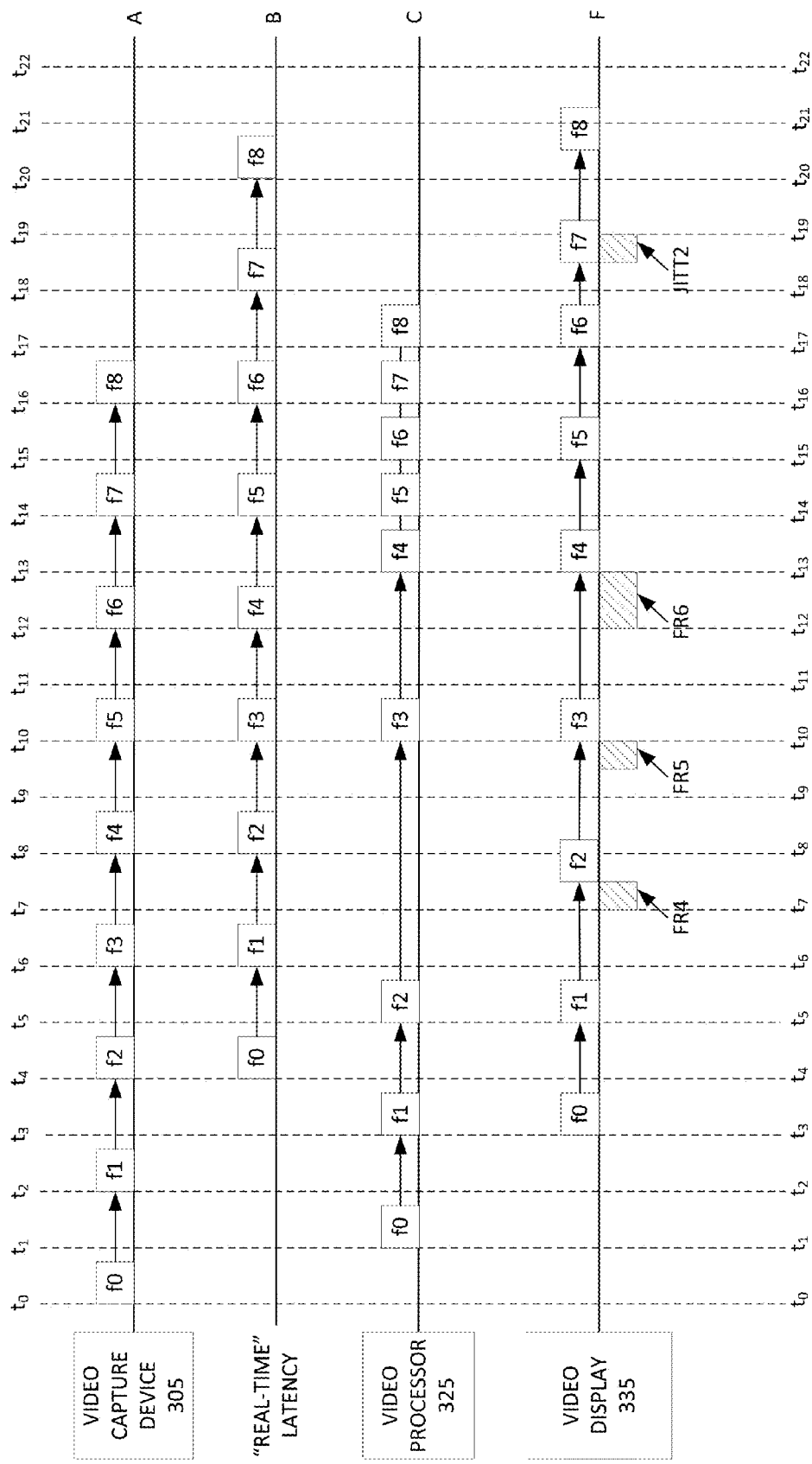
FIG. 5 is a timing diagram schematically illustrating a video processing control scheme in accordance with at least one exemplary embodiment of the present disclosure.

Referring now to FIG. 5, a timing diagram schematically illustrating a video processing control scheme in accordance with various exemplary embodiments of the present disclosure is shown. Abscissas A and B of FIG. 5 illustrate transmission of image frames (f0-f8) from a video capture device such as, for example, video capture device 305 of FIG. 3, and an exemplary real-time arrival of frames f0-f8 at an exemplary display device. The timing in Abscissas A and B of FIG. 5 is identical to that of Abscissas A and B of FIG. 4, and therefore, they are not explained here.

Abscissa C illustrates an exemplary timing at which image frames f0-f8 arrive at an exemplary video processor according to the present disclosure (e.g., video processor 325 of FIG. 3). The timing illustrated in Abscissa C of FIG. 5 is identical to the timing illustrated in Abscissa C of FIG. 4.

Abscissa F illustrates a timing at which image frames f0-f8 may be provided by video processor 325 to a video display such as, for example, video display 335 of FIG. 3, in accordance with an exemplary embodiment of the present disclosure. In particular, video processor 325 provides image frames for display to video display 335 based on the number of image frames accumulated at video processor 325, or stored at a video data buffer (not shown) accessible to video processor 325. Abscissa B illustrates a real-time latency of four image frames. In accordance with an exemplary embodiment of the present disclosure, video processor 325 provides image frames to video display 335 depending on how many image frames have been accumulated at video processor 325 and how that amount compares to a desired image-frame latency, which may be set, for example, to be around the real-time latency illustrated in Abscissa B. For the exemplary embodiment, and for simplicity of illustration, the desired number of accumulated image frames is two image frames.

It is noted that the exemplary embodiment and the following description are provided for descriptive purposes, and a person having ordinary skill in the art would understand that embodiments according to the present disclosure may be implemented differently, and may also be optimized for a particular application. A person having ordinary skill in the art would also understand that the present disclosure is directed to applications in which a display rate may reach thousands of image frames per second, and a real-time latency (which will be described in further detail below) may comprise the timing for displaying hundreds of image frames (instead of the two to four image frames used in the description).

At time unit $t_1$ in FIG. 5, video processor 325 receives image frame f0. At time unit $t_3$, with image frame f0 accumulated at video processor 325, video processor 325 receives image frame f1. Thus, in view of the accumulation of two image frames, video processor 325 provides image frame f0 to video display 335 at time unit $t_3$.

At time unit $t_5$, video processor 325 receives image frame f2. Accordingly, in view of accumulation of image frames f1 and f2, video processor 325 provides image frame f1 to video display 335 and sets a current display rate of one image frame every two time units.

At time unit $t_7$, which would correspond to the display of the next image frame based on the current display rate, video processor 325 has yet to receive image frame f3. This may be due to, for example, bandwidth or other network issues. According to the exemplary embodiment, and because video processor 325 has one image frame, f2, accumulated, video processor 325 reduces its video display rate. For example, in the illustration of FIG. 5, video processor 325 reduces the video display rate from one image frame every two time units to one image frame every two and one half time units, and provides image frame f2 for display at the mid-point between time units $t_7$ and $t_8$. Although this creates an image freeze before image f2 is displayed, illustrated in Abscissa F as FR4, the image freeze is relatively short, e.g., the length of one half of a time unit long, and thus can be less noticeable by a user than the image freezes illustrated in Abscissas D and E of FIG. 4. A shorter image freeze period provides for a smoother video on video display 335 than the video on video display 435 provided by the conventional configurations described with respect to FIG. 4.

It is noted that reducing the display rate from one image frame every two time units to one image frames every two and one half time units has been selected for the present exemplary embodiment for illustrative purposes only, and the timing and magnitude of a rate reduction for an embodiment according to the present disclosure need not be derived from what has been illustrated in Abscissa F with respect to the present exemplary embodiment. A person having ordinary skill in the art would understand that a rate reduction or increase according to the present disclosure may vary based on a multitude of factors from one implementation to another, and may even vary within a single implementation.

Continuing with Abscissa F of FIG. 5, at time unit $t_{10}$, which would correspond to the display of the next image frame based on the current image display rate of one image frame every two and one half time units, video processor 325 receives image frame f3. Thus, image frame f3 is the only image frame accumulated at video processor 325. According to the present disclosure, because the number of accumulated images is below the desired level of two image frames, but there is an accumulated image, video processor 325 maintains the current display rate and provides image frame f3 for display to video display 335. Although maintaining the current display rate produces a second image freeze, illustrated in Abscissa F as FR5, this image freeze is also one half of a time unit long, and thus, less noticeable by a user than those illustrated in Abscissas D and E of FIG. 4.

At the mid-point between time unit $t_{12}$ and $t_{13}$, which would correspond to the display of the next image frame based on the current display rate, video processor 325 has yet to receive image frame f4. According to the exemplary embodiment, and because video processor 325 does not have an image frame accumulated, video processor 325 waits for image frame f4 to arrive. At time unit $t_{13}$, which is one half of a time unit after image frame f4 was scheduled for display based on the current display rate, video processor 325 receives image frame f4. According to the exemplary embodiment, video processor 325 provides image frame f4 to video display 335 at time unit $t_{13}$. Although this creates an image freeze, illustrated in Abscissa F as FR6, the image freeze is the length of one time unit, and thus, less noticeable by a user than some of the image freezes illustrated in Abscissas D and E (i.e., FR1 in Abscissa D and FR3 in Abscissa E).

At time unit $t_{14}$, video processor 325 receives image frame f5, and thus, it has accumulated image frame f5. Then, at time unit $t_{15}$, video processor 325 receives image frame f6, and thus, it has accumulated image frames f5, and f6. According to the present disclosure, because the number of accumulated images has reached the desired level (i.e., two image frames), video processor 325 updates its display rate to one image frame every two time units. Thus, at the time unit $t_{15}$, which would correspond to the time to display the next image frame based on the current image display rate, video processor 325 provides image frame f5 to video display 335.

At time unit $t_{16}$, video processor 325 receives image frame f7, and thus, it has accumulated image frames f6 and f7. According to the present disclosure, because the number of accumulated images has reached the desired level (i.e., two image frames), video processor 325 maintains its current display rate to one image frame every two time units.

At time unit $t_{17}$, video processor 325 receives image frame f8, and thus, it has accumulated image frames f6, f7, and f8. According to the present disclosure, because the number of accumulated images has exceeded the desired level of two image frames, video processor 325 increases the display rate to one image frame every one and one half time units. Also at time unit $t_{17}$, video processor 325 provides image frame f6 to video display 335, according to the previous display rate of one frame every two time units.

At the mid-point between time unit $t_{18}$ and $t_{19}$, which corresponds to the display of the next image frame based on the current display rate, video processor 325 provides image frame f7 to video display 335, leaving only image frame f8 accumulated at video processor 325. According to the present disclosure, because the number of accumulated images is at the desired level of two image frames video processor 325 decreases the display rate to one frame every two time units and provides image frame f7 for display to video display 335. As illustrated by jitter period JITT2, the previous display rate produces image jitter. However, because this image jitter is caused by a controlled increase in rate, it is over a shorter time period and may be less noticeable to a user than the jitter JITT1 illustrated in Abscissa D of FIG. 4 because the configuration corresponding to Abscissa E drops image frames, it does not exhibit jitter.

As illustrated in FIG. 5, exemplary embodiments of the present disclosure control and vary the output of video frames from a buffer to the display in a manner that balances providing a smooth display in a real-time image rendering environment. In particular, under the exemplary timing for receiving image frames from a video capture device illustrated in Abscissa C of FIGS. 4 and 5, exemplary embodiments provide a relatively smooth and accurate display of the captured video via smaller freeze and/or jitter periods than those of conventional configurations, for example, as schematically illustrated in Abscissa D.

One having ordinary skill in the art would recognize that FIG. 5 is for illustrative purposes only, and that the behavior of an exemplary video processor according to the present disclosure may vary based on a number of conditions. For example, an exemplary video processor according to the present disclosure may drop a received image frame if the image frame is not available for display after a predetermined period of time has elapsed, or may limit the maximum decrease and/or increase of the display rate based on accumulated image frame data, without departing from the scope of the present disclosure.

Figure 6:
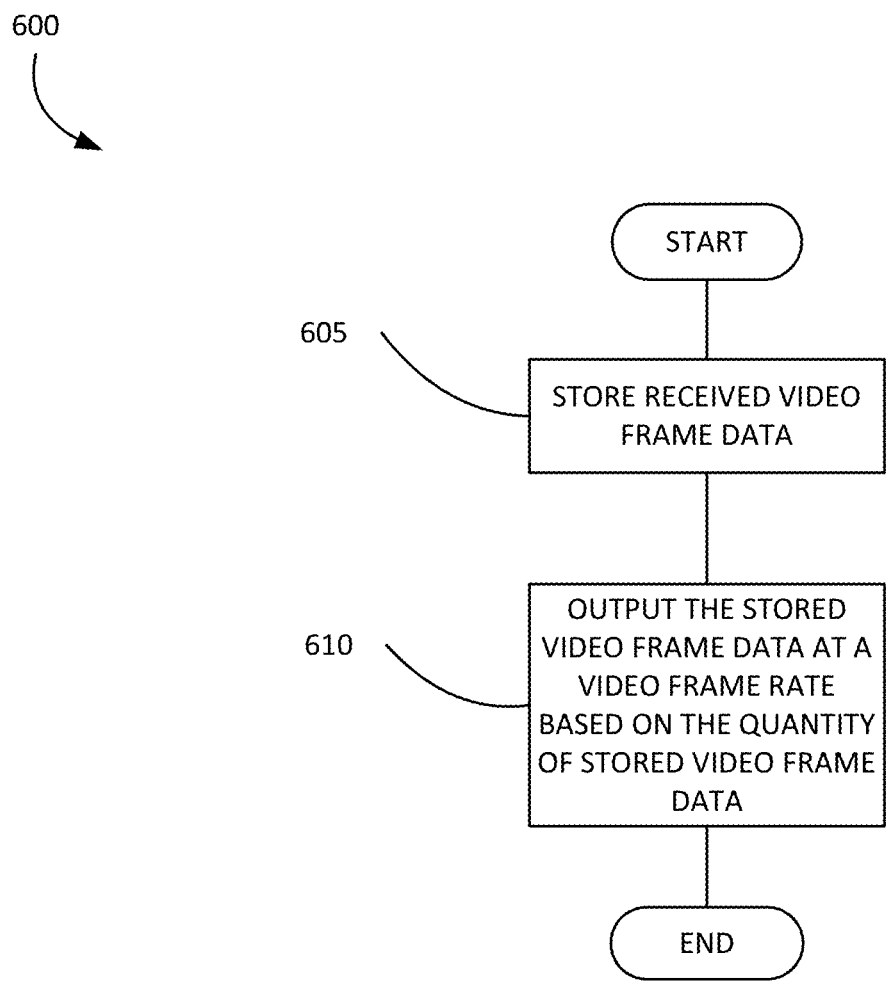
FIG. 6 is a flow diagram depicting a method for processing video in accordance with at least one exemplary embodiment of the present disclosure.

FIG. 6 is a flow diagram depicting a method for processing video in accordance with at least one exemplary embodiment. At step 605, the method includes storing video frame data captured at a site in real-time. The video frame data may include data corresponding to a portion of an image frame or may include one or more image frames. In an exemplary embodiment, the video frame data may be stored in a storage buffer, for example, that is part of a video processing device or accessible by the video processing device.

At step 610, the method includes outputting the stored video frame data at a video frame rate based on the quantity of video frame data stored at step 605. The stored video frame data may be output, for example, from a video processing device to a display device, and such display device may be part of the video processing device or accessible by the video processing device. Thus, in accordance with various exemplary embodiments, a quantity of video frame data may be stored and monitored in a storage buffer, and information about the quantity of video frame data may be used to modify an output rate for outputting the video frame data to a display device.

Figure 7:
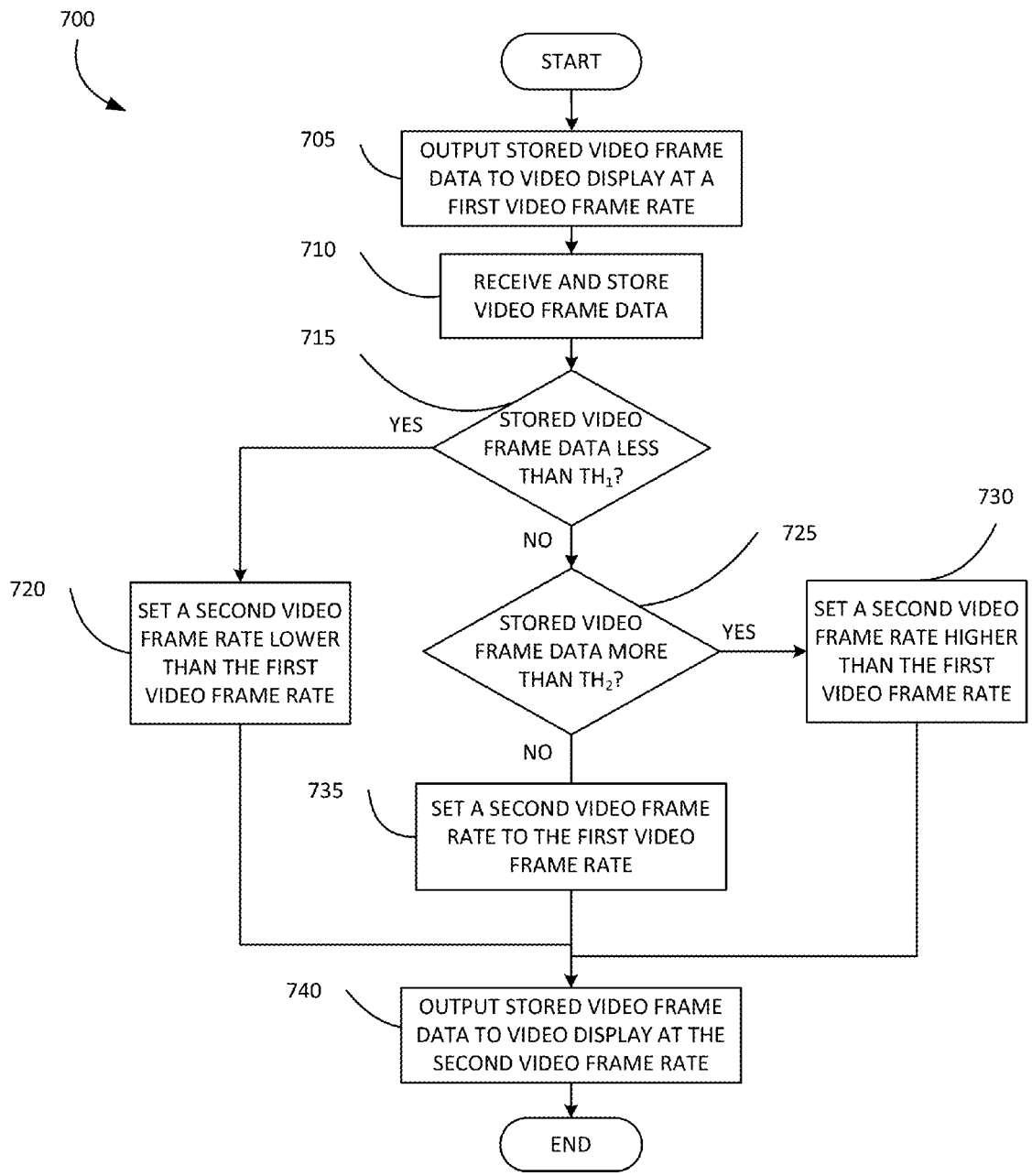
FIG. 7 is a flow diagram depicting a method for processing video in accordance with at least one exemplary embodiment of the present disclosure.

FIG. 7 is a flow diagram depicting a video processing method in accordance with at least one exemplary embodiment. At step 705, the method includes outputting stored video frame data at a first video frame rate. In an exemplary embodiment, the stored video frame data may be data stored in a storage buffer, for example, that is part of a video processing device or accessible by the video processing device. The stored video frame data may be output, for example, from the video processing device to a display device, and such display device may be part of the video processing device or accessible by the video processing device.

According to various exemplary embodiments of the present disclosure, the first video frame rate may be similar to the video frame rate at which the corresponding video frames were captured by a video frame capture device. The first video frame rate, however, may be set according to one or more of the following manners: a predetermined and/or application-based rate; a negotiated rate between the video frame capture device and the exemplary embodiment; a latency along a communication path between the video frame capture device and the exemplary embodiment; or a bandwidth limitation for transferring video frames along a communication path between the video frame capture device and the exemplary embodiment.

For example, the video frame capture device may be capable of providing a relatively high video frame rate of high resolutions images. However, the bandwidth allocated for communication between the video frame capture device and the exemplary embodiment may not allow for transfer of high resolution frames at the high video frame rate, or the network latency may be too high to maintain the high video frame rate of the high resolution video frames while providing a real-time playback of the video frames. Accordingly, the video frame capture device may be configured by a user, or automatically by negotiation with the exemplary embodiment, to reduce its video frame capture rate, reduce the resolution of some or all of the captured video frames, or both.

However, the present disclosure is not so limited and the first video frame rate and/or the resolution of the video frames may be substantially different from that used by the image capture device. For example, the exemplary embodiment may process and combine image frames to realize a video frame rate that may be higher or lower than the video frame capture rate, which may be accomplished using image processing methods and techniques generally known to persons having ordinary skill in the art without departing from the scope of the present disclosure. The exemplary embodiment may also, or in the alternative, use image processing methods to increase or reduce the resolution of some or all video frames without departing from the scope of the present disclosure.

Furthermore, the designation of the video frame rate at step 705 as a first video frame rate is not intended as a limitation regarding the illustrated video processing method at a particular stage of operation of the exemplary embodiment. For example, the first video frame rate may be the video frame rate set during initial operation of the exemplary embodiment, or may be a video frame rate determined after extensive operation of the exemplary embodiment.

At step 710, the method includes receiving and storing video frame data in a storage buffer. The received video frame data may be received, for example, from a video capture device. Furthermore, the received video frame data may be received from the video capture device through, for example, a communication link and a data communications network.

At step 715, the method includes comparing a quantity of video frame data stored at the storage buffer to a first threshold, $TH_1$. If the quantity of stored video frame data is less than $TH_1$, at step 720 second video frame rate is set that is lower than the first video frame rate. If, on the other hand, the quantity of stored video frame data is not less than $TH_1$, the method includes comparing the quantity of video frame data stored at the storage buffer to a second threshold, $TH_2$, at step 725 the quantity of stored video frame data is more than $TH_2$, at step 730 the second video frame rate is set to be higher than the first video frame rate.

At step 735, if the quantity of stored video frame data is not less than $TH_1$ (as determined in step 715), and is not more than $TH_2$ (as determined in step 725), the method includes setting the second video frame rate to be the first video frame rate. At step 740, the method includes outputting the stored video frame data at the second video frame rate. The stored video frame data may be output, for example, from the video processing device to the display device referenced with respect to step 705 above.

Thus, in accordance with various exemplary embodiments, a quantity of video frame data received from a video capture device and stored at a storage buffer may be monitored, and an output rate for outputting the stored video frame data from the storage buffer to a display device may be adjusted based on the quantity of stored video frame data. In particular, if the quantity of stored video frame data is less than a first threshold, then the video frame rate for outputting stored video frame data may be reduced. The reduction may allow more time for video frame data transmitted from the video capture device, which may have been delayed by, for example, a node of a communication network, to arrive to, and be stored and accumulated at, the storage buffer. The additional time may reduce the probability of a storage underflow, and thus, of a "frozen" display, and may also reduce the probability of a video frame data being dropped for not arriving within a maximum latency period. This may enhance the smoothness, and thus, the quality and fidelity of a real-time video playback.

Furthermore, if the quantity of stored video frame data is more than a second threshold, which may be the same or higher than the first threshold, then the video frame rate for outputting stored video frame data may be increased. The increase may reduce the quantity of stored video frame data in the storage buffer and prevent a storage overflow, which may be caused by a burst of video frame data arriving from the video capture device through the communication network. This reduces the probability of image frames being dropped due to a storage overflow. Furthermore, the increase may reduce the latency of displaying the images from when they were captured. This too may enhance the smoothness, and thus, the quality and fidelity of a real-time video playback.

Further still, if the quantity of stored video frame data is more than the first predetermined threshold, but less than the second predetermined threshold, then the video frame rate is set to a video frame rate similar to that at which the video frames were captured. In an exemplary embodiment, the video frame rate at which the video frames were captured is known, and if the quantity of stored video frame data is more than the first predetermined threshold, but less than the second predetermined threshold, then the video frame rate for displaying the video frames may be set to the video frame rate at which the video frames were captured.

For simplicity, the above description relies on the use of two thresholds for setting and controlling the output video frame rate, but the present disclosure is not so limited, and may rely on more or less thresholds than those set forth above. For example, an exemplary embodiment may rely on only one threshold and be configured to increase the output video frame rate when the quantity of stored video frame data exceeds the one threshold and to decrease the output video frame rate when the quantity of stored video frame data is less than the one threshold, without departing from the scope of the present disclosure.

Furthermore, for simplicity, the above description does not describe how much the output video frame rate is either increased or decreased based on the amount of stored video frame data. However, a person having ordinary skill in the art would understand that the magnitude of the increase or decrease may be predetermined, based on the implementation/application, based on the difference between the amount of stored video frame data and the corresponding threshold, or even optimized based on network conditions, without departing from the scope of the present disclosure.

Figure 8:
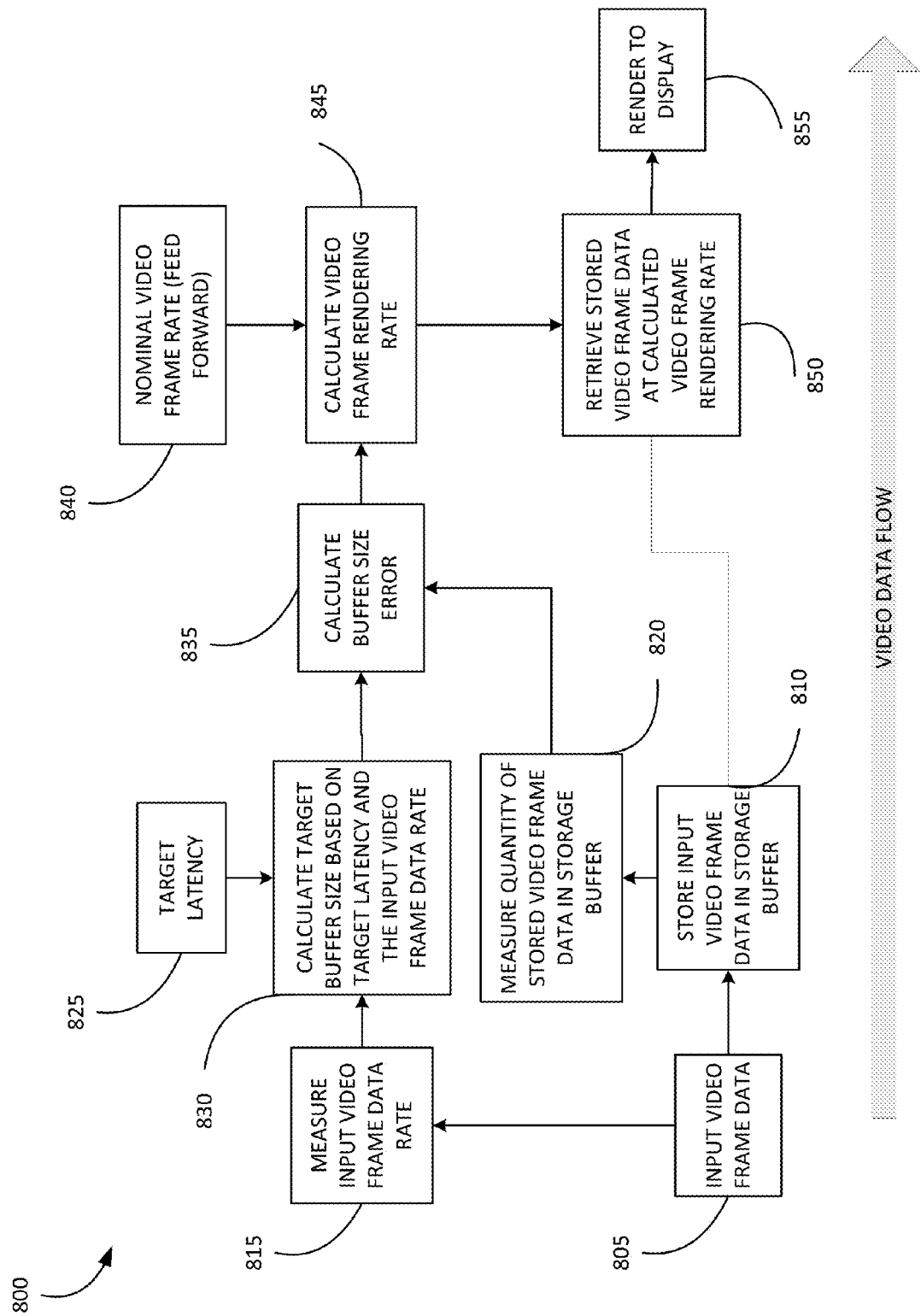
FIG. 8 is a functional block diagram depicting a control scheme for video processing in accordance with at least one exemplary embodiment of the present disclosure.

FIG. 8 is a functional block diagram schematically depicting an exemplary control scheme by which to monitor and vary the rendering of captured video frame data to a display in accordance with various exemplary embodiments of the present disclosure. Those having ordinary skill in the art will appreciate that one or more of the functional blocks need not be performed in carrying out a control scheme in accordance with the present disclosure, and modifications can be made without departing from the scope of the present disclosure.

At functional block 805 input video frame data. Input video frame data comprises data associated with video frames captured by a video capture device (not shown) which have been captured at a video frame capture rate. The video capture device and/or the site at which the video frames are being captured may be located remotely from where a system in accordance with the exemplary embodiment receives the input video frame data.

The input video frame data is then stored at functional block 810 in, for example, a storage buffer, in accordance with various exemplary embodiments of the present disclosure. The video frame data rate of the input video frame data is measured, as shown at functional block 815. The measuring of the input video frame data rate permits a determination of the number of video frames that have been received, how much video time corresponds to the received video frames, a determination if any video frames are missing, and the amount of video frame data that has been received. Functional block 820 illustrates that a measurement is made of the quantity of stored video frame data that has been received and is presently stored in the storage buffer.

A target latency period is provided at functional block 825. In various exemplary embodiments according to the present disclosure, target latency relates to an amount of video time that is targeted to be stored in the storage buffer according to the present disclosure; this target latency can be determined by selecting a latency that sufficiently maintains a real-time video display of the received and stored input video frame data. In various exemplary embodiments of the present disclosure the target latency may relate to the total latency between a video frame being captured and the video frame being displayed or it may relate only to the latency between the receiving of a video frame at the video processing system and the displaying of the particular video frame. Furthermore, in various exemplary embodiments of the present disclosure, the target latency may be a configuration parameter set for a particular application, or may be instead a variable parameter configurable by a user or based on network/system conditions.

Functional block 830 illustrates calculating a target buffer size based on the target latency provided at functional block 825 and on a measure of the input video frame data rate at functional block 815. As noted above, functional block 815 measures the video frame data rate of the input video frame data to determine how many video frames have been received and how much video frame data has been received. Functional block 830 uses the measurements calculated at functional block 815 and the target latency provided by block 825 to calculate how much input video frame data stored in the storage buffer corresponds to a time substantially similar to the target latency. In other words, functional block 830 calculates a target buffer size based on the target latency and an input video frame data rate.

For example, functional block 815 may indicate to functional block 830 that the input video frame data rate is 30 video frames per second and that each video frame, either on average or individually, comprises 50 kB of data. Furthermore, functional block 825 may provide a target latency of 0.5 seconds. According to various exemplary embodiments of the present disclosure, functional block 830 calculates a target buffer size as follows:

30 video frames/sec×0.5 sec×50 kB/video frame=750 kB.

Thus, according to the exemplary figures above, the target buffer size would be 750 kB according to the exemplary embodiment above.

Functional block 835 illustrates a function of calculating a buffer size error. In accordance with various exemplary embodiments of the present disclosure, a buffer size error comprises a difference between the quantity of stored video frame data stored in the storage buffer, as measured at functional block 820, and the target buffer size, as calculated at functional block 830. Thus, according to the exemplary parameters above, a buffer size error comprises a difference between the quantity of stored video frame data provided by functional block 820 and 750 kB.

Functional block 840 provides a nominal video frame rate. In accordance with various exemplary embodiments of the present disclosure, the nominal video frame rate corresponds to a video frame capture rate at which the input video frames were captured by a video capture device (not shown). However, the present disclosure is not so limited, and the nominal video frame rate may correspond to a current video frame rate at which input video frames are being provided/rendered to a display.

Functional block 845 illustrates a function of calculating a video frame rendering rate. In accordance with various exemplary embodiments of the present disclosure, functional block 845 receives the nominal video frame rate from functional block 840 and the calculated buffer size error 835 to calculate a video frame rendering rate. According to the present disclosure, the calculated video frame rate may be such that the resulting video may be considered a real-time representation of the captured video with minimum or no fidelity issues (e.g., with minimum or no freeze or jitter).

Functional block 850 illustrates retrieving video frames (i.e., video frame data) from the storage buffer at the video frame rendering rate calculated at functional block 845. At functional block 855, the retrieved video frames are provided to a display device (not shown).

In accordance with various exemplary embodiments of the present disclosure, it is desirable that a rate at which the exemplary embodiment renders video frames for display to a display device (not shown) is identical, or substantially similar, to a video frame capture rate at which the video frames were captured at a remote location. A noticeable difference between these two rates may lead to image jitter and it is therefore undesirable.

However, certain conditions may affect the transmission of video frame data through a path between the remote location and the various exemplary embodiments. These conditions may cause video frame data to arrive with significant delay and/or may in bursts. In accordance with various exemplary embodiments of the present disclosure, a video frame rendering rate is calculated on functional block 845 based on a nominal video frame rate provided by functional block 840 and a buffer size error calculated on functional block 835 to provide a smooth real-time rendering of input video frame data captured at a remote location. The buffer size error is calculated based on a target latency provided by functional block 825 and the amount of video frame data stored at a storage buffer. Therefore, in accordance with various exemplary embodiments of the present disclosure, the real-time rendering of video frames captured at a remote location is managed to reduce noticeable display abnormalities (e.g., image freeze and image jitter) that may occur along the transmission path between the remote location and the exemplary embodiment.

Figure 9:
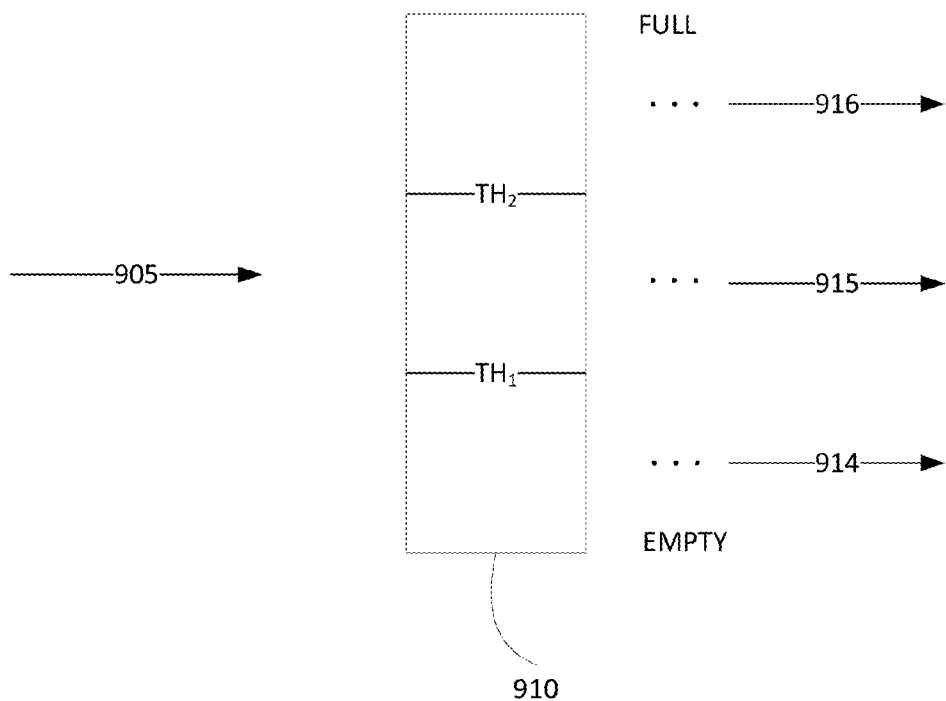
FIG. 9 is a schematic representation of a video storage buffer according to at least one exemplary embodiment of the present disclosure.

FIG. 9 is a schematic representation of a video storage buffer, showing the input and output of video frame data, illustrative of an exemplary embodiment of the present disclosure. More specifically, FIG. 9 illustrates the capacity of a video storage buffer 910 according to various exemplary embodiments. Input video frame data 905 is received and stored at storage buffer 910.

As illustrated and described with respect to FIGS. 4 and 5, real-time video frame data may encounter delays along a transmission path, and thus, may arrive inconsistently at the storage buffer 910, which may be logically coupled to a video processor (such as video processor 325 of FIGS. 3 and 5) from a video capture device. When video frame data is delayed, the quantity of video frame data stored at storage buffer 910 is reduced as the video processor continues to retrieve video frame data stored at video storage buffer 910 and output the video frame data 915 to display at a consistent rate. If video storage buffer 910 becomes empty, no video frame data is available for display, thus, the display of the corresponding video will freeze with the last video frame data displayed.

When video frame data are received and stored at video storage buffer 910 as a burst (for example, because some of the video frame data are delayed, as explained above, and arrive as part of a burst with more timely video frame data), the quantity of image frame data stored at video storage buffer 910 increases. If the storage buffer 910 becomes full, no more image frames may be stored, and thus, image frame data may need to be dropped. Thus, various exemplary embodiments of the present disclosure may decrease or increase the rate at which video frame data is retrieved from video storage buffer 910 to control the amount of data at storage buffer 910 to maintain a smooth video playback to a user while maintaining a real-time latency.

In particular, with reference to FIG. 9, input video frame data 905 is stored in storage buffer 910 by a video processor according to an exemplary embodiment of the present disclosure (not shown), and provided to a display device (not shown) as output video frame data 915 for video playback of a corresponding video. According to various exemplary embodiments of the present disclosure, if the quantity of stored video frame data is between threshold levels $TH_1$ and $TH_2$, video processor may maintain the rate for output video frame data 915 at a rate similar to that at which the stored video frame data was captured by a video capture device (not shown).

If input video frame data 905 is delayed along the communication path between the video capture device (not shown) and storage buffer 910, then the quantity of video frame data stored at video storage buffer 910 is reduced, and may become less than $TH_1$ as the video processor continues to retrieve and provide output video frame data 915 to the display device (not shown). According to various exemplary embodiments of the present disclosure, if the quantity of stored video frame data becomes less than threshold $TH_1$, then the output video frame data may be reduced, as shown at 914, for example, to a predetermined rate which is lower than the rate at which the stored video frame data was captured by the video capture device (not shown). Alternatively, the output video frame data at 914 may be at a variable rate which is lower than the rate at which the stored video frame data was captured and varies based on the quantity of stored video frame data. By way of example, a rate decrease may be proportional to the decrease in stored video frame data.

On the other hand, if input video frame data 905 is received and stored at video storage buffer 910 as a burst (for example, because some of the video frame data that has been delayed, as explained above, is now arriving at the same time as other more timely-received video frames), the quantity of video frame data stored at video storage buffer 910 may increase and become more than $TH_2$. According to various exemplary embodiments of the present disclosure, if the quantity of stored video frame data becomes more than $TH_2$, then the video frame rate for providing output video frame data may be increased, as depicted at 916, for example, to a predetermined rate which is higher than the rate at which the stored video frame data was captured by the video capture device (not shown). Alternatively, the output video frame data at 916 may be at a variable rate which is higher than the rate at which the stored video frame data was captured and varies based on the quantity of stored video frame data. By way of example, a rate increase may be proportional to the increase in stored video frame data.

Accordingly, in various exemplary embodiments of the present disclosure, the quantity of stored video frame data is controlled to remain between thresholds $TH_1$ and $TH_2$. Based on the selections for the thresholds $TH_1$ and $TH_2$, various embodiments of the present disclosure can control a latency between the capture and the display of video frames of a video stream between a video capture device and a video display device.

For example, according to the various exemplary embodiments of the present disclosure, a latency between the capture and the display of a particular video frame includes a transfer period between the capture of the particular video frame by the video capture device and the storage of the particular video frame in a storage buffer, such as storage buffer 910 of FIG. 9. Also, there is a storage period between the storage of the particular video frame in storage buffer 910 and the display of the particular video frame in the display device. The various embodiments of the present disclosure control the storage period by controlling the video frame rate for providing video frames to a display device based on the quantity of video frame data in storage buffer 910.

Furthermore, to satisfy a real-time display of the video frames, various exemplary embodiments of the present disclosure may be configured to maintain a quantity of stored video frame data such that the average latency between the capture and display of video frames is appropriate for the real-time video needs of the particular application. In various exemplary embodiments of the present disclosure, the average latency may be controlled by adjusting the thresholds $TH_1$ and $TH_2$ to create a storage period which, when added to the average transfer period (and any other periods between the capture and display of a video frame), the total latency is sufficient for real-time applications.

By way of example, and not as limitation, for applications in which a target latency between the capture and the display of a video frame may be 0.5 seconds, and the average transfer delay is 0.2 second, thresholds $TH_1$ and $TH_2$ may be selected to maintain a target storage period of 0.3 seconds. Accordingly, for example, $TH_1$ may be set to a quantity of video frame data corresponding to 0.2 seconds and $TH_2$ may be set to a quantity of video frame data corresponding to 0.4 seconds. Therefore, various embodiments of the present disclosure modify the rate for providing video frames to a display device to maintain the quantity of video frame data at about 0.3 seconds (between 0.2 seconds and 0.4 seconds), and maintain the average latency at about 0.5 seconds (average transfer period of 0.2 seconds plus average storage period of 0.3 seconds).

For example, for an implementation in which the average video frame is of a size of 100 kB, and in which a video frame capture rate is 24 images/second:

$$TH1=0.2 \text{ sec}*24 \text{ images/sec}*100 \text{ kB/image}=480 \text{ kB};$$
and $$TH2=0.4 \text{ sec}*24 \text{ images/sec}*100 \text{ kB/image}=960 \text{ kB}.$$

Accordingly, to maintain an average latency of 0.3 seconds, an exemplary embodiment of the present disclosure, as explained with reference to FIG. 9, may set the thresholds $TH_1$ and $TH_2$ as calculated above. The figures above are exemplary, and various exemplary embodiments of the present disclosure may be set differently. For example, $TH_1$ may be set to a quantity of video frame data corresponding to 0.1 seconds and $TH_2$ may be set to a quantity of video frame data corresponding to 0.3 seconds. Therefore, the various embodiments of the present disclosure would modify the rate for providing video frames to a display device to maintain the quantity of video frame data at about 0.2 seconds (between 0.1 seconds and 0.3 seconds), and more aggressively maintain the average latency at about 0.4 seconds (0.1 second less than the target latency of 0.5 seconds). Furthermore, the difference between the target storage period and one or both of the thresholds may be different from that set forth above without departing from the teachings of the present disclosure.

Figure 10:
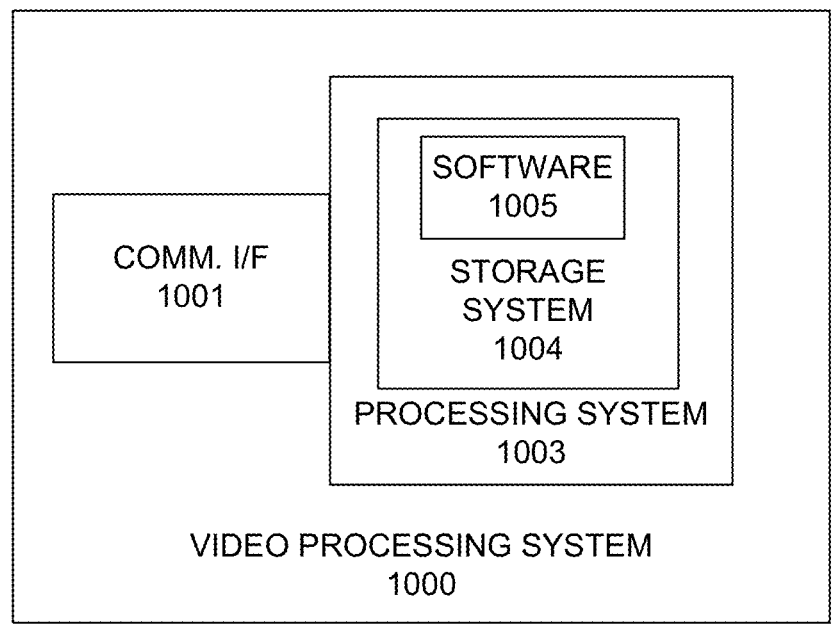
FIG. 10 schematically illustrates a video processing system according to at least one exemplary embodiment of the present disclosure.

FIG. 10 illustrates an exemplary embodiment of a video processing system according to the present disclosure. Video processing system 1000 is an example of video processor 325, although a person having ordinary skill in the art would recognize that a video processor according to the present disclosure may be configured differently. Video processor 1000 comprises communication interface 1001 and processing system 1003. Processing system 1003 is linked to communication interface 1001. Processing system 1003 includes processing circuitry and storage system 1004 that stores software 1005. Video processor 1000 may include other well-known components such as a power system, a battery, and/or an enclosure that are not shown for clarity.

Communication interface 1001 comprises at least communication circuitry to interface with devices external to video processing system 1000, and may include circuitry for wired and/or wireless communication. Furthermore, communication interface 1001 may be configured to communicate with a storage buffer area for implementing elements of the present disclosure, such as storage buffer 910 described above, and/or with a display device for implementing elements of the present disclosure, as described above. Communication interface 1001 may also include a memory device, software, processing circuitry, or some other communication device.

Processing system 1003 may comprise a microprocessor and other circuitry that retrieves and executes software 1005 from storage system 1004. Storage system 1004 comprises a disk drive, flash drive, data storage circuitry, or some other memory apparatus. Storage system 1004 may include storage buffer area for implementing elements of the present disclosure, such as storage buffer 910 described above. Processing system 1003 is typically mounted on a circuit board that may also hold storage system 1004 and/or portions of communication interface 1001. Software 1005 comprises computer programs, firmware, or some other form of machine-readable processing instructions. Software 1005 may include an operating system, utilities, drivers, network interfaces, applications, or some other type of software.

When executed by processing system 1003, software 1005 directs processing system 1003 to operate video processor 1000 as described herein for video processor 325.

Figure 11:
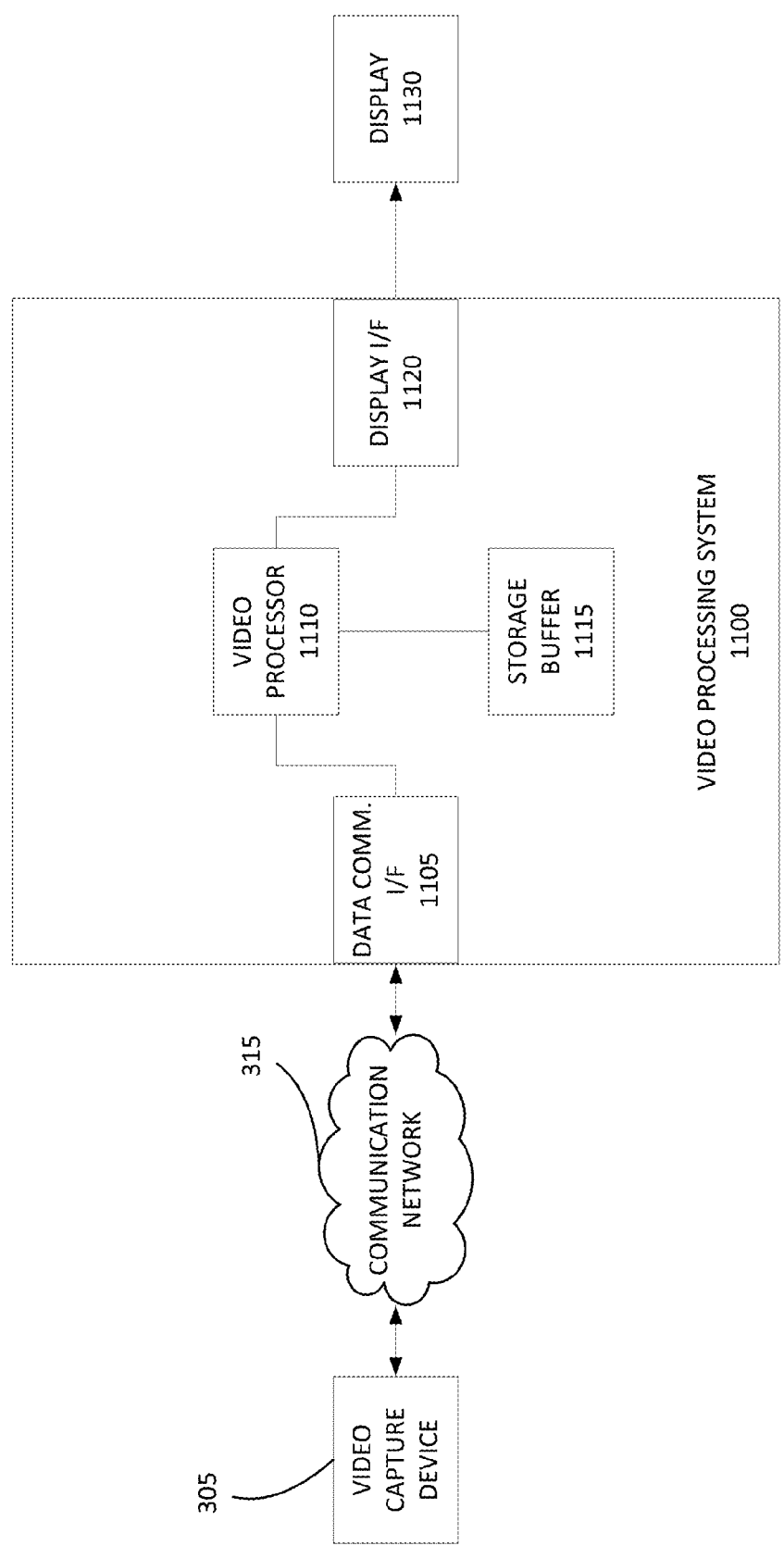
FIG. 11 schematically illustrates a video processing system according to at least one exemplary embodiment of the present disclosure.

FIG. 11 illustrates an exemplary embodiment of the present disclosure. FIG. 11 includes system 1100, which includes a data communication interface 1105, a processor 1110, a storage buffer 1115, and a display device interface 1120. FIG. 11 further includes display 1130. Video processing system 1100 and display 1130 may be embodied within robotic surgical system 100 depicted in FIG. 1 and described above, but the present disclosure is not so limited, and these elements may be embodied in systems for applications other than remotely-controlled surgery. FIG. 11 further includes video capture device 305 and communication network 315, which have been described with respect to FIG. 3, and such description will not be repeated herein for brevity.

During a remotely-controlled surgical procedure, video capture device 305 captures images at a surgical site at a first image frame rate. Image frame data associated with the captured images is transmitted through communication network 315 to video processing system 1100 for display at, for example, surgeon console 110 described above with respect to FIG. 1. Video processing system receives the image frame data through data communication interface 1105 and the image frame data is stored at storage buffer 1115. Processor 1110 determines the quantity of image frame data stored at storage buffer 1115 and compares this quantity to one or more thresholds, as described above with respect to FIG. 7. Processor 1110 further determines a second image frame rate based on the comparison and provides image frame data to display interface 1120 for display on display monitor 1130, as has been described with respect to various embodiments above, and in particular, with respect to FIGS. 6 and 7.

The embodiments can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to effect the various responses and signal processing in accordance with various exemplary embodiments of the present disclosure can be implemented by a processor of or in conjunction with the electronics/control console 115, such as an electrosurgical processing unit discussed above, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

As described above, the methods and systems in accordance with various exemplary embodiments can be used in conjunction with a surgical instrument having an end effector configured to perform multiple surgical procedures via components that are actuated via a transmission mechanism at the proximal end of the instrument. Further, according to an aspect of the embodiments, any combinations of the described features, functions and/or operations can be provided.

Other embodiments of the invention will be apparent to those skilled in the art from consideration of the specification and practice of the present disclosure and claims herein. It is intended that the specification and examples be considered as exemplary only, with a true scope and spirit of the invention being indicated by the following claims.

What is claimed is:

1. A method for processing video, comprising:
    storing, at a video data buffer, an input video frame data, wherein the input video frame data comprises image frames recorded at an image frame capture rate; and
    outputting stored video frame data from the video data buffer at an output video frame rate by varying the output video frame rate relative to a nominal output video frame rate, the varying being based on at least the amount of video frame data stored at the video data buffer, the nominal output video frame rate being set to be substantially equal to the image frame capture rate, wherein,
    if the amount of video frame data stored at the video data buffer is lower than a threshold, then the outputting of the stored video frame data comprises outputting the stored video frame data at an output video frame rate that is lower than the nominal output video frame rate by a first predetermined rate difference, and
    if the amount of video frame data stored at the video data buffer is higher than the threshold, then the outputting of the stored video frame data comprises outputting the stored video frame data at an output video frame rate that is higher than the nominal output video frame rate by a second predetermined rate difference.

2. The method of claim 1, wherein if the amount of video frame data stored at the video data buffer is higher than the threshold, then the outputting of the stored video frame data comprises outputting the stored video frame data at an output video frame rate that is higher than the nominal output video frame rate.

3. The method of claim 2, wherein the nominal output video frame rate is set to a current output video frame rate.

4. The method of claim 1, wherein if the amount of video frame data stored at the video data buffer is higher than a threshold, then the outputting of the stored video frame data comprises outputting the stored video frame data at an output video frame rate that is higher than the nominal output video frame rate.

5. The method of claim 1, wherein:
    if the amount of video frame data stored at the video data buffer is lower than the threshold, then the outputting of the stored video frame data comprises outputting the stored video frame data at an output video frame rate that is lower than the nominal output video frame rate by a rate difference proportional to the difference between the threshold and the amount of video frame data stored at the video data buffer; and
    if the amount of video frame data stored at the video data buffer is higher than the threshold, then the outputting of the stored video frame data comprises outputting the stored video frame data at an output video frame rate that is higher than the nominal output video frame rate by a rate difference proportional to the difference between the amount of video frame data stored at the video data buffer and the threshold.

6. The method of claim 1, wherein:
    if the amount of video frame data stored at the video data buffer is higher than a second threshold, then the outputting of the stored video frame data comprises outputting the stored video frame data at an output video frame rate that is higher than the nominal output video frame rate; and
    the threshold is lower than the second threshold.

7. The method of claim 6, wherein if the amount of video frame data stored at the video data buffer is higher than the first threshold and lower than the second threshold, then the outputting of the stored video frame data comprises outputting the stored video frame data at the nominal output video frame rate.

8. The method of claim 7, wherein:
    the threshold comprises an amount of data corresponding to a number of image frames recorded at the image frame capture rate for a first predetermined period of time, wherein the first predetermined period of time is less than a latency period; and
    the second threshold comprises an amount of data corresponding to a number of image frames recorded at the image frame capture rate for a second predetermined period of time, wherein the second predetermined period of time is more than the latency period.

9. The method of claim 8, wherein:
    the latency period is 500 milliseconds.

10. The method of claim 1 wherein:
if the amount of video frame data stored at the video data buffer is higher than a second threshold, then the outputting of the stored video frame data comprises outputting the stored video frame data at an output video frame rate that is higher than the nominal output video frame rate by a predetermined rate difference; and
the threshold is lower than the second threshold.

11. The method of claim 10, wherein if the amount of video frame data stored at the video data buffer is higher than the threshold and lower than the second threshold, then the outputting of the stored video frame data comprises outputting the stored video frame data at the nominal output video frame rate.

12. The method of claim 1, wherein:
if the amount of video frame data stored at the video data buffer is lower than the threshold, then the outputting of the stored video frame data comprises outputting the stored video frame data at an output video frame rate that is lower than the nominal output video frame rate by a rate difference proportional to the difference between the first threshold and the amount of video frame data stored at the video data buffer;
if the amount of video frame data stored at the video data buffer is higher than a second threshold, then the outputting of the stored video frame data comprises outputting the stored video frame data at an output video frame rate that is higher than the nominal output video frame rate by a rate difference proportional to the difference between the amount of video frame data stored at the video data buffer and the second threshold; and
the threshold is lower than the second threshold.

13. The method of claim 12, wherein if the amount of video frame data stored at the video data buffer is higher than the threshold and lower than the second threshold, then the outputting of the stored video frame data comprises outputting the stored video frame data at the nominal output video frame rate.

14. The method of claim 1, wherein outputting stored video frame data from the video data buffer at an output video frame rate comprises outputting the stored video frame data to a display interface.

15. The method of claim 1, wherein storing the input video frame data comprises storing input video frame data associated with images of a surgical site recorded by an endoscopic camera.

16. A method for processing video, comprising:
capturing image frames by an image frame capture device;
storing, at a video data buffer, an input video frame data, wherein the input video frame data comprises the captured image frames; and
outputting stored video frame data from the video data buffer at an output video frame rate by varying the output video frame rate based on at least an amount of video frame data stored at the video data buffer and on a predetermined latency range, wherein
the varying comprises decreasing the output video frame rate to maintain the predetermined latency range, and
the predetermined latency range is set to enable approximately real-time display of the captured image frames relative to the capturing of the images frames.

17. The method of claim 16, wherein outputting stored video frame data from the video data buffer at an output video frame rate by varying the output video frame rate based on at least the amount of video frame data stored at the video data buffer further comprises decreasing the output video frame rate to maintain an average latency within the predetermined latency range.

18. The method of claim 16, wherein the predetermined latency range comprises zero to 1.5 seconds.

* * * * *